(12) United States Patent
Eury

(10) Patent No.: US 10,610,657 B2
(45) Date of Patent: Apr. 7, 2020

(54) SEALING CUSHION AND PATIENT INTERFACE DEVICE EMPLOYING SAME

(71) Applicant: KONINKLIJKE PHILIPS N.V., Eindhoven (NL)

(72) Inventor: Matthew Paul Eury, Latrobe, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1381 days.

(21) Appl. No.: 14/401,335

(22) PCT Filed: May 6, 2013

(86) PCT No.: PCT/IB2013/053598
§ 371 (c)(1),
(2) Date: Nov. 14, 2014

(87) PCT Pub. No.: WO2013/171617
PCT Pub. Date: Nov. 21, 2013

(65) Prior Publication Data
US 2015/0144140 A1    May 28, 2015

Related U.S. Application Data

(60) Provisional application No. 61/647,626, filed on May 16, 2012.

(51) Int. Cl.
*A61M 16/06* (2006.01)
(52) U.S. Cl.
CPC ........ *A61M 16/0622* (2014.02); *A61M 16/06* (2013.01); *A61M 16/0616* (2014.02); *A61M 16/0633* (2014.02); *A61M 16/0683* (2013.01)

(58) Field of Classification Search
CPC .......... A61M 16/0611; A61M 16/0622; A61M 2016/0661; A62B 18/02; A62B 18/025
USPC ..................................................... 128/206.24
See application file for complete search history.

(56) References Cited

U.S. PATENT DOCUMENTS

| | | | |
|---|---|---|---|
| 4,677,977 A * | 7/1987 | Wilcox | A62B 18/025 128/206.24 |
| 5,540,223 A * | 7/1996 | Starr | A61M 16/06 128/205.25 |
| 5,647,357 A * | 7/1997 | Barnett | A61M 16/06 128/205.25 |
| 7,992,560 B2 | 8/2011 | Burton | |

(Continued)

FOREIGN PATENT DOCUMENTS

| | | | |
|---|---|---|---|
| GB | 2412594 | * 10/2005 | ............ A61M 16/06 |
| JP | 2011056286 A | 3/2011 | |

(Continued)

OTHER PUBLICATIONS

Shore Hardness Chart (Year: 2017).*

*Primary Examiner* — Timothy A Stanis
*Assistant Examiner* — Victoria Murphy
(74) *Attorney, Agent, or Firm* — Michael W. Haas

(57) ABSTRACT

A cushion (44) for a patient interface device (26) that has an inverted geometry. In particular, the cushion includes a support portion (56) having a first edge (60) and a second edge (62) located opposite the first edge, and a sealing flap (58) extending in a cantilevered fashion inwardly from an inner edge of the second edge of the support portion and toward the longitudinal axis (59) of the cushion.

14 Claims, 9 Drawing Sheets

(56) References Cited

U.S. PATENT DOCUMENTS

| | | | | |
|---|---|---|---|---|
| 2003/0089372 A1* | 5/2003 | Frater | ............... | A61M 16/06 128/206.24 |
| 2006/0130844 A1* | 6/2006 | Ho | ............... | A61M 16/06 128/206.24 |
| 2008/0302366 A1* | 12/2008 | McGinnis | ............ | A61M 16/06 128/206.24 |

FOREIGN PATENT DOCUMENTS

| | | |
|---|---|---|
| JP | 05912250 B2 | 4/2016 |
| WO | WO0197893 A1 | 12/2001 |
| WO | WO2006069345 A2 | 6/2006 |
| WO | WO2008094924 A1 | 8/2008 |
| WO | WO2012025843 A1 | 3/2012 |

\* cited by examiner

SEALING CUSHION AND PATIENT INTERFACE DEVICE EMPLOYING SAME

CROSS-REFERENCE TO RELATED APPLICATIONS

This patent application claims the priority benefit under 35 U.S.C. § 371 of international patent application no. PCT/IB2013/053598, filed May 6, 2013, which claims the priority benefit under 35 U.S.C. § 119(e) of U.S. Provisional Application No. 61/647,626 filed on May 16, 2012, the contents of which are herein incorporated by reference.

BACKGROUND OF THE INVENTION

1. Field of the Invention

The present invention pertains to patient interface devices structured to deliver a flow of breathing gas to a user, and, in particular, to a sealing cushion for a patient interface device that has an inverted geometry as compared to traditional cushions wherein a sealing flap portion of the cushion is located on the inside of a support portion of the cushion.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. This interface should be comfortable and maintain a robust seal while at the same time not creating air-path restrictions and/or increased difficulty in breathing. In addition, the sealing cushion should be comfortable enough to ensure patient compliance, but must also be stable and consistently provide a seal for compliance. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

One known mask geometry that is commonly used is shown in FIG. 1A. As seen in FIG. 1A, that mask geometry employs a cushion assembly 2 that includes a cushion member 4 coupled to a support ring 6 (which facilitates connection of cushion assembly 2 to a rigid or semi-rigid faceplate or shell). Cushion member 4 includes a bottom portion 8 coupled to support ring 6, wherein bottom portion 8 also includes an outer wall 10. In addition, cushion member 4 also includes a support portion 12 structured to provide a support function for cushion assembly 2, and a sealing flap 14, structured to provide a suitable seal against the user's face during use.

As seen in FIG. 1A, sealing flap 14 and support portion 12 are integrated as two features within the same component, and support portion 12 is located on the inside of sealing flap 14. In other words, sealing flap 14 is located above and outside the inner support portion 12. In this configuration, sealing flap 14 must be made long enough ($L_1$ in FIG. 1A) to cover support portion 12, and thus sealing flap 14 requires an additional length $L_2$ as compared to support portion 12 to ensure that it extends out over support portion 12. This extra flap length increases part height, results in unnecessary additional length in the sealing flap, and often times undesirably encroaches over the user's nares at the nostril area cushion assembly 4 during use. The extra flap length also often causes undesirable bunching of sealing flap 14 while in engagement with the user's face, which may cause leak paths, visual obstruction to the user, and general annoyance and comfort issues. As used herein, bunching shall refer to an area where, when the cushion is donned by the user, extra sealing flap length collects and folds/curls over itself, resulting in bunches or folds of sealing flap (as shown in FIG. 1B). These areas of bunching also result in zones which are at risk to compliance issues (wherein compliance is expressed as $\Delta V/\Delta P$ (the change in volume divided by the change in pressure). Cushion assembly 2 also requires a curved, cantilever style support portion 12 inside sealing flap 14 to achieve a compressible and soft, yet supportive inner support structure, and it is this curved, cantilever style support portion 12 that causes the issue just described.

SUMMARY OF THE INVENTION

Accordingly, it is an object of the present invention to provide a cushion for a patient interface device that overcomes the shortcomings of conventional cushions. This object is achieved according to one embodiment of the present invention by providing cushion that is inverted as compared to the traditional geometry described elsewhere herein such that a sealing flap of the cushion is located on the inside of a support portion of the cushion.

In one embodiment, a cushion for a patient interface device is provided that includes a support portion having a bottom edge and an engagement edge located opposite the bottom edge, the bottom edge lying in a first plane, the engagement edge being structured to engage a face of a user when the patient interface device is donned by the user, wherein the engagement edge extends at an angle with respect to a second plane that is parallel to the first plane that is less than or equal to +30 degrees and greater than or equal to −30 degrees. The cushion also includes a sealing flap extending in a cantilevered fashion inwardly from an inner edge of the engagement edge of the support portion and toward a longitudinal axis of the cushion, wherein a length of the sealing flap measured from a proximal end thereof to a distal end thereof is 15 mm or less.

In another embodiment, a cushion for a patient interface device is provided that includes a support portion having a first edge, a second edge located opposite the first edge, and a cantilevered portion that extends outwardly from an outer edge of the second edge in a direction away from a longitudinal axis of the cushion, the cantilevered portion and the second edge being structured to engage a face of a user when the patient interface device is donned by the user. The cushion also includes a sealing flap extending in a cantilevered fashion inwardly from an inner edge of the second edge of the support portion and toward the longitudinal axis of the cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1A:
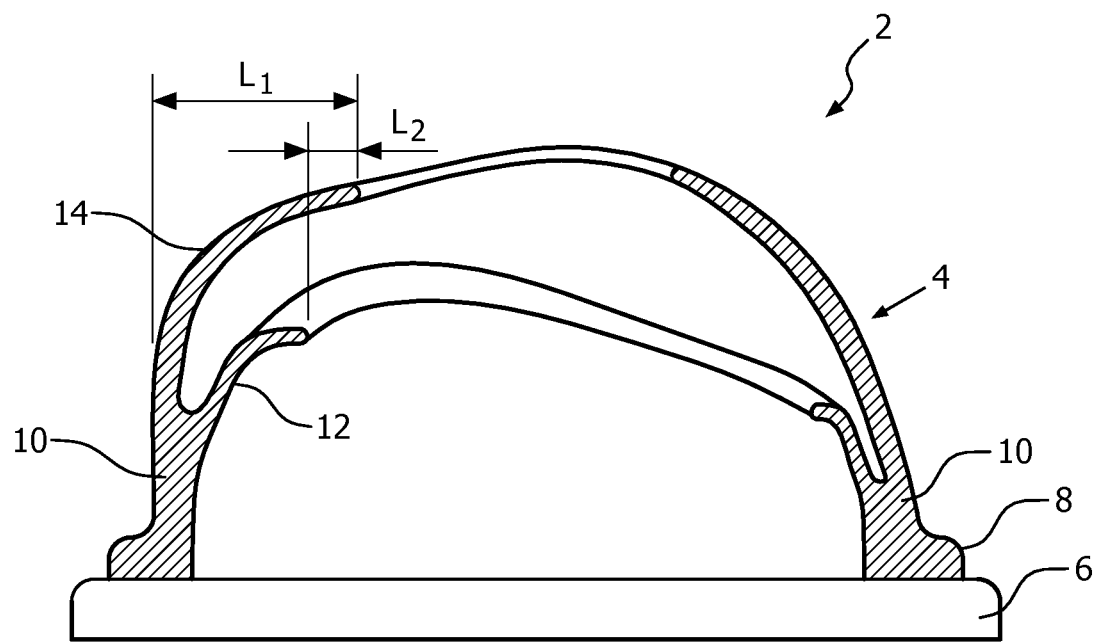
FIGS. 1A and 1B are a cross-sectional and schematic views, respectively, of a cushion assembly used in a known, prior art mask geometry.
Figure 1B:
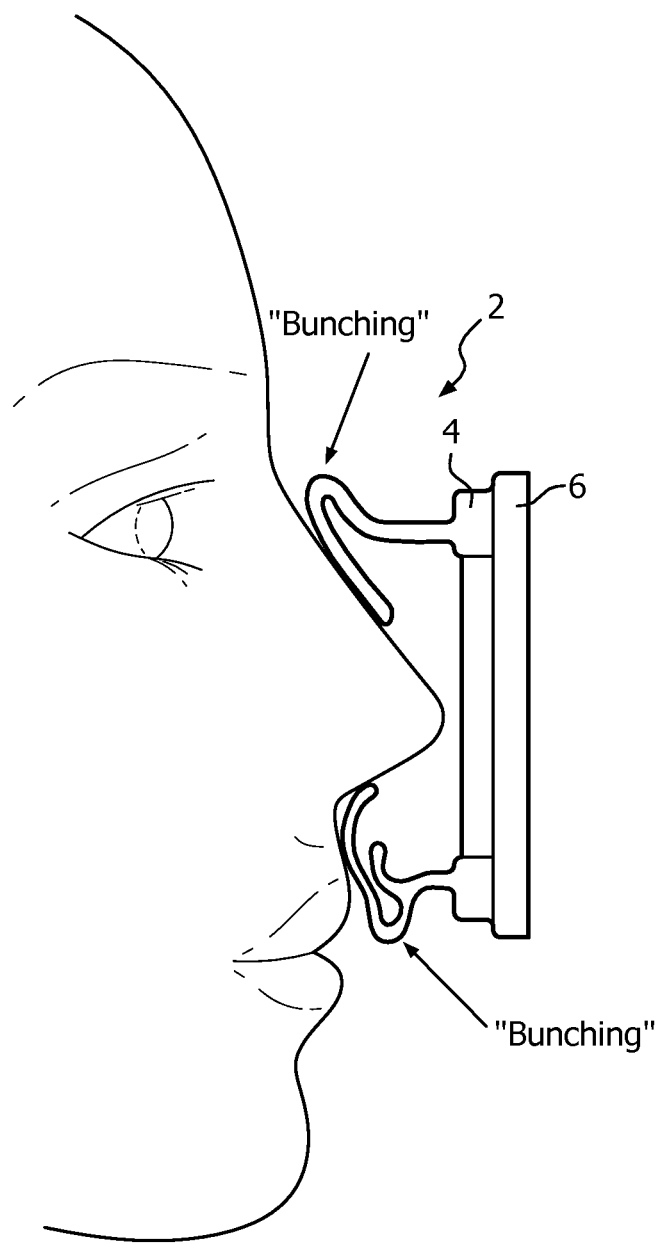

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
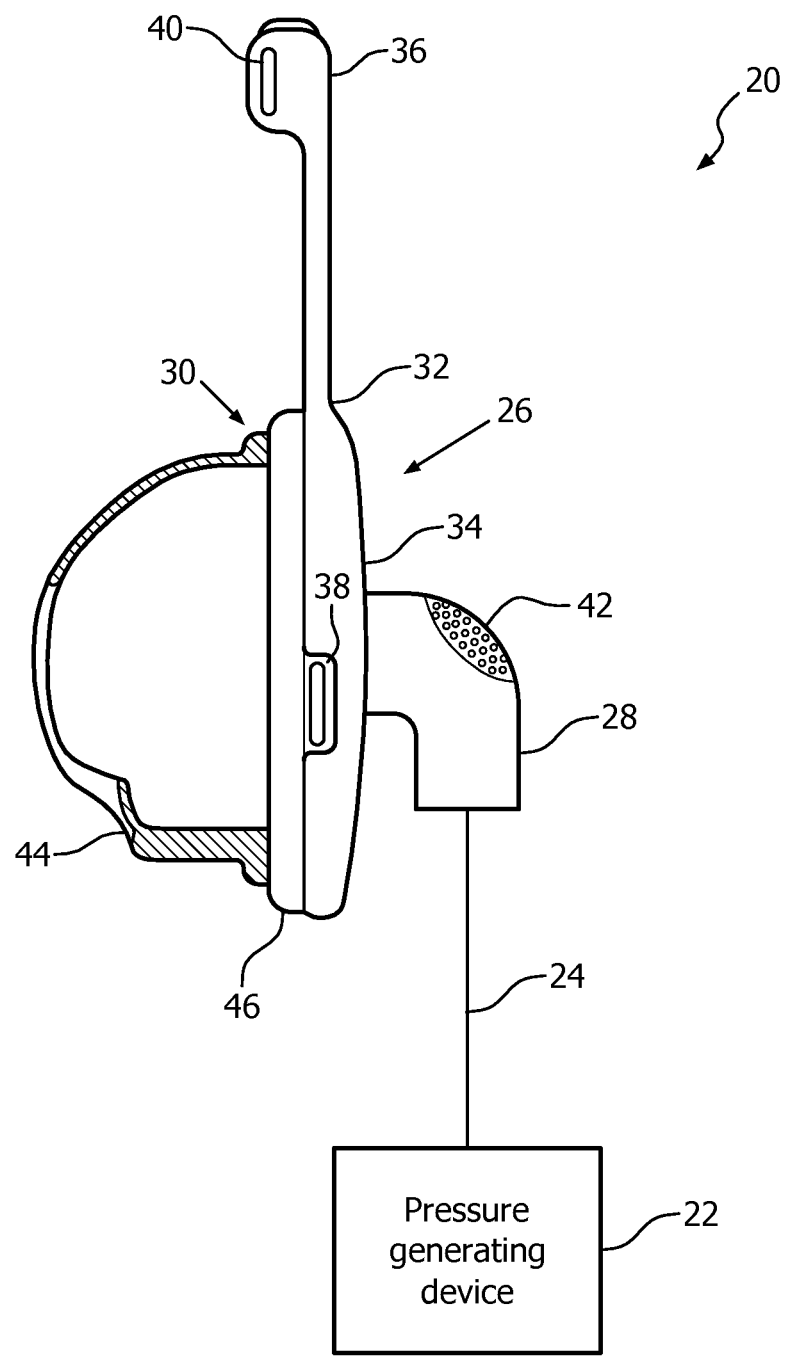
FIG. 2 is a schematic diagram of a system adapted to provide a regimen of respiratory therapy to a patient according to one exemplary embodiment of the invention.

A system 20 adapted to provide a regimen of respiratory therapy to a patient according to one exemplary embodiment of the invention is generally shown in FIG. 2. System 20 includes a pressure generating device 22, a delivery conduit 24, and a patient interface device 26 including an elbow conduit 28. Pressure generating device 22 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 24 is structured to communicate the flow of breathing gas from pressure generating device 22 to patient interface device 26.

In the illustrated embodiment, patient interface device 26 comprises a nasal mask structured to cover the nose of the patient. However, other types of patient interface devices 26, such as, without limitation, a nasal/oral mask that covers the patient's nose and mouth, or a full face mask that covers the patient's face, which facilitates the delivery of the flow of breathing gas to, and the removal of a flow of exhalation gas from, the airway of a patient may be used while remaining within the scope of the present invention.

In the embodiment shown in FIG. 2, patient interface device 26 includes a cushion assembly 30 (shown in partial cross-section in FIG. 2), and a frame member 32 having a faceplate portion 34 and a forehead support portion 36. In the illustrated embodiment, frame member 32 is made of a rigid or semi-rigid material, such as, without limitation, an injection molded thermoplastic or silicone. Straps (not shown) of a headgear component may be attached to faceplate portion 34 via attachment members 38 and to forehead support portion 36 via attachment members 40 to secure patient interface device 26 to the patient's head. An opening in faceplate portion 34 to which elbow conduit 28 is coupled allows the flow of breathing gas from pressure generating device 22 to be communicated to an interior space defined by faceplate portion 34 and cushion assembly 30, and then, to the airway of a patient. The opening in faceplate portion 34 also allows the flow of exhalation gas (from the airway of such a patient) to be communicated to exhaust vent 42 provided in elbow conduit 28.

Figure 3:
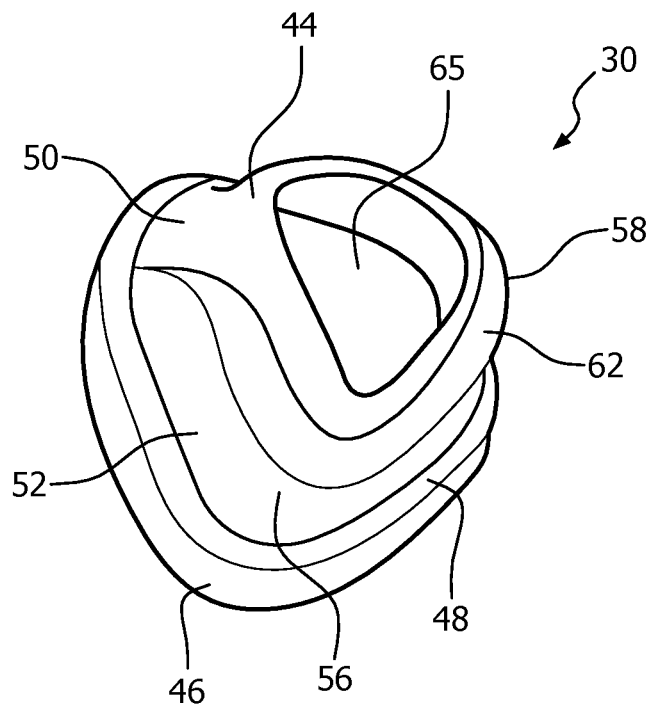
FIG. 3 is an isometric view.
Figure 4:
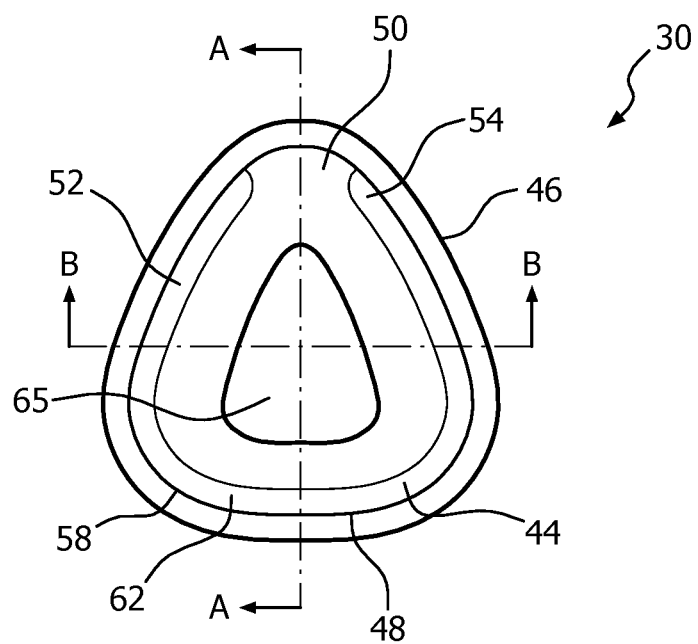
FIG. 4 is a front plan view.
Figure 5:
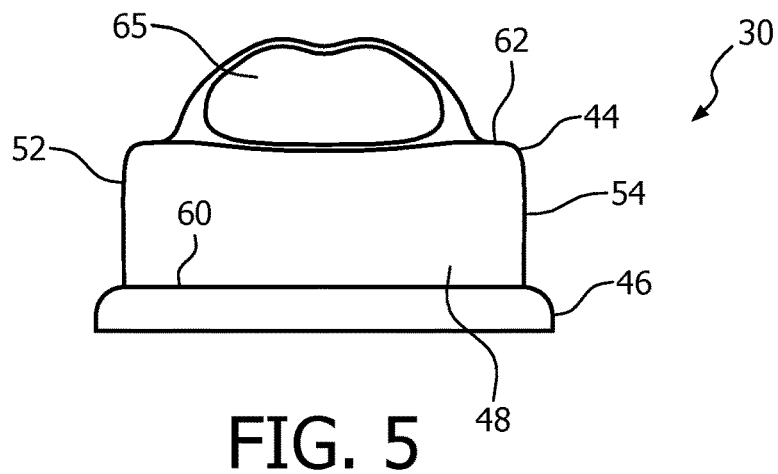
FIG. 5 is a bottom elevational view of a cushion assembly of a patient interface device of the system of FIG. 2.
Figure 6:
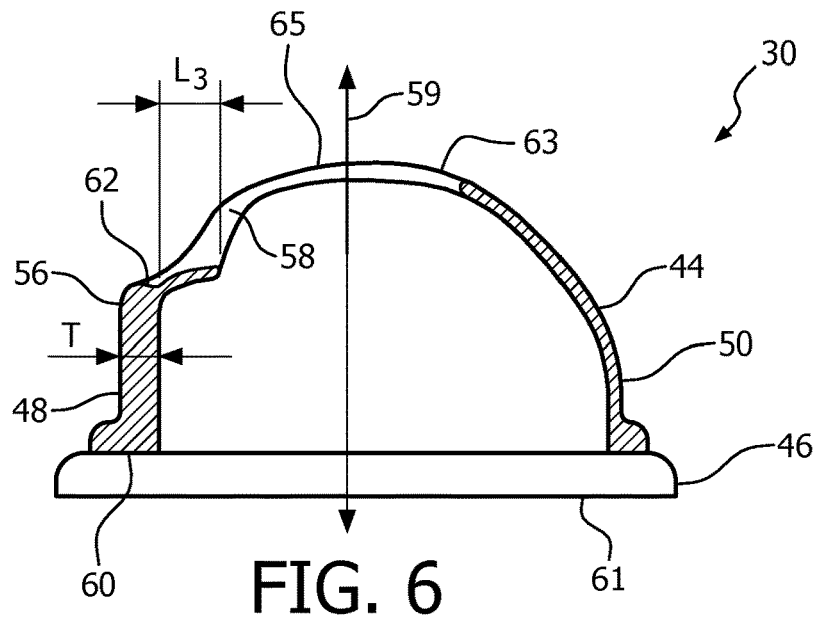
FIG. 6 is a cross-sectional view of the cushion assembly of FIG. 4 taken along lines A-A of FIG. 4
Figure 7:
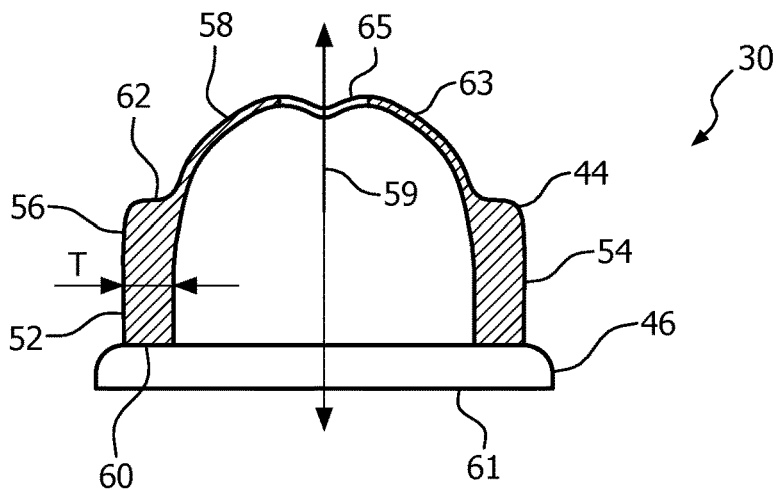
FIG. 7 is a cross-sectional view of the cushion assembly of FIG. 4 taken along lines B-B of FIG. 4.

FIG. 3 is an isometric view, FIG. 4 is a front plan view, and FIG. 5 is a bottom elevational view of cushion assembly 30 according to the exemplary embodiment. In addition, FIG. 6 is a cross-sectional view of cushion assembly 30 taken along lines A-A of FIG. 4 and FIG. 7 is a cross-sectional view of cushion assembly 30 taken along lines B-B of FIG. 4. Cushion assembly 30 includes a cushion member 44 coupled to a support ring 46. Support ring 46 is made from a rigid or semi-rigid material, such as, without limitation, an injection molded thermoplastic or silicone, and facilitates secure fluid connection of cushion assembly 30 to frame member 32.

In the exemplary embodiment, cushion member 44 is defined from a unitary piece of soft, flexible, cushiony, elastomeric material, such as, without limitation, silicone, an appropriately soft thermoplastic elastomer, a closed cell foam, or any combination of such materials. Also in the exemplary embodiment, cushion assembly 30 has a generally triangular shape including a bottom region 48, an apex region 50 located opposite bottom region 48, a first side region 52 and a second side region 54 located opposite first side region 52. As a result, both cushion member 44 and support ring 46 will have associated bottom, apex and first and second side regions.

Cushion member 44 is inverted as compared to the traditional geometry described elsewhere herein. In particular, cushion member 44 includes a support portion 56 and a sealing flap 58, wherein sealing flap 58 is located on the inside of support portion 56 closer to a longitudinal axis 59 (FIGS. 6 and 7) of cushion assembly 30 (longitudinal axis 59 extends from the rear 61 of cushion assembly 30 where cushion assembly 30 attaches to frame member 32 to the front 63 of cushion assembly 30, and thus defines the general direction in which gasses flow through cushion assembly 30). In other words, support portion 56 is located below and outside of the inner sealing flap 58. Sealing flap 58 extends in an angled (e.g. upwardly), cantilevered fashion from support portion 56 and defines an orifice 65 structured to receive the nose of the user. As described in greater detail herein, this inverted geometry creates minimal landing on the user's face while achieving contact of support portion 56 and a sealing flap 58, all without encroaching the nares, thereby leaving a free and clear air path.

As seen in FIGS. 3 and 4, support portion 56 in the exemplary embodiment comprises an outer wall of cushion member 44 that extends outwardly from support ring 46 (i.e., generally parallel to longitudinal axis 59 and generally perpendicular to the plane defining rear 61 of cushion member 44 where cushion member 44 attaches to support ring 46). In addition, in the exemplary embodiment, support portion 56 extends along first side region 52, bottom region 48, and second side region 54. Support portion 56 includes a bottom edge 60 that is adjacent and directly coupled to support ring 46, and a top engagement edge 62 located opposite bottom edge 60. Engagement edge 62 is structured to engage the face of the user when patient interface device 26 is donned by the user. In particular, in the present embodiment, the portion of engagement edge 62 at first side region 52 will engage one cheek of the user, the portion of engagement edge 62 at bottom region 48 will engage the region between the upper lip and nose of the user, and the portion of engagement edge 62 at second side region 54 will engage the other cheek of the user. In the exemplary embodiment, support portion 56 including engagement edge 62 is made of a material having a durometer of 00 to 60 on the Shore 00 scale, and has a thickness (T in FIGS. 6 and 7) of 2 mm to 15 mm.

In addition, because support portion 56 is located below and outside of the inner sealing flap 58, engagement edge 62 is able to have a flatter profile than exists in the prior art. In particular, engagement edge 62 extends inwardly (toward the center of orifice 65) in a generally linear fashion at an angle with respect to a second plane that is parallel to the plane defining rear 61 of cushion member 44, wherein that angle is less than or equal to +30 degrees and greater than or equal to −30 degrees. In one particular exemplary embodiment, engagement edge 62 is "substantially flat," which as used herein shall mean that it extends inwardly in a generally linear fashion at an angle with respect to the second plane that is less than or equal to +5 degrees and greater than or equal to −5 degrees (i.e., it inclines or declines no more than 5 degrees in either direction).

Furthermore, by positioning sealing flap 58 inside of support portion 56, sealing flap 58 is able to be made much shorter than prior art sealing flaps. This is true because sealing flap 58 does not need to be long enough to curve out and over an inner support cushion to achieve a seal like traditional designs. In one particular exemplary embodiment, the length, $L_3$ (FIG. 6), of sealing flap 58, measured from the proximal end thereof where it is connected to support portion 56 to the distal end thereof (which defines orifice 65), is 15 mm or less. In another particular exemplary embodiment, the length, $L_3$, of sealing flap 58 measured as just described is 5 mm or less. The short length of sealing flap 58 minimizes, and in some cases eliminates, the possibility of undesirable bunching of sealing flap 58. The short length of sealing flap 58 also reduces the likelihood that sealing flap 58 will undesirably encroach on the nares of the user during use.

Moreover, the longer sealing flap lengths employed in traditional designs makes such designs susceptible to compliance ($\Delta V/\Delta P$) and pulsing and/or flexing of the sealing flap during use. The relatively short length of sealing flap 58 (due to the inverted geometry) as described above may decrease compliance ($\Delta V/\Delta P$), especially when utilizing a more flexible and thinner sealing flap as described below. This is true because less sealing flap length results in less area, and as a result less potential for excessive compliance (i.e., change in volume under pressure) that could cause issues with comfort and performance due to extreme stretching of the soft material and risk of tear or a burst of the sealing flap as it could stretch beyond its ultimate stress and elongation. The reduction of compliance would also result in less dynamic pulsing of cushion assembly 30 and flexing of sealing flap 58, which occurs in pressure support therapy during inspiratory positive airway pressure (IPAP) and expiratory positive airway pressure (EPAP). All of the aforementioned is especially true at higher pressures such as >20 $cmH_2O$.

In addition, the geometry of cushion member 44 with the relatively shorter length of sealing flap 58 allows for the use of much more flexible and softer materials with a much higher elongation and stretch ratio in the sealing flap 58. In particular, the material may have a durometer of 00-60 Shore 00 and/or an elongation of approximately 500-1500%. The geometry of cushion member 44 also allows for a reduced thickness of sealing flap 58, which in the exemplary embodiment is 0.20 mm to 2 mm. Furthermore, when using a softer and extremely flexible material with a high elongation as just described, the thickness of sealing flap 58 may 0.20 mm to 0.40 mm. Such thicknesses would otherwise not be possible without the geometry described herein including short sealing flap 58, since a sealing flap having the combination of such a reduced thickness and such a soft and elastic material would not hold its shape and geometry if it were of the traditional longer length (it would deform and sag under its own weight). Also, such a traditional length sealing flap made form such a soft and elastic material would stretch too much and have a undesirably large compliance ($\Delta V/\Delta P$). In contrast, the shorter length of sealing flap 58 as described herein with the soft and elastic materials as just described allows such a thin flap to retain its geometry without stretching too much and without having an undesirably large compliance.

Figure 8:
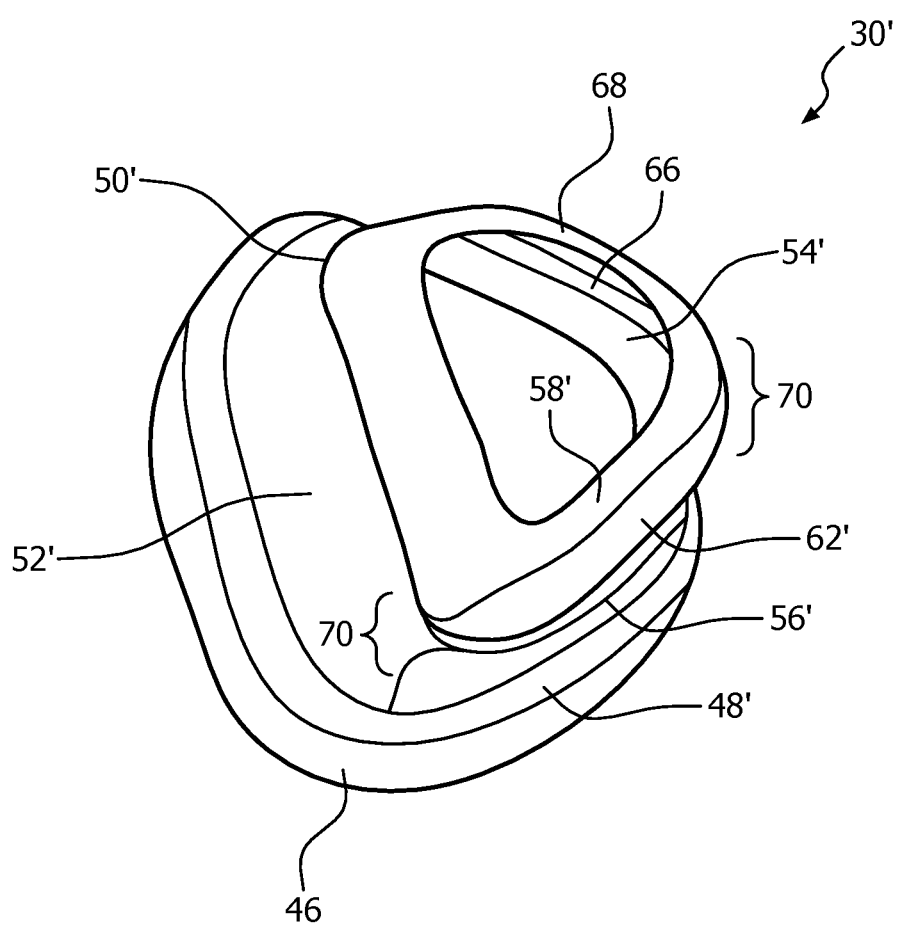
FIG. 8 is an isometric view of a cushion assembly according to an alternative exemplary embodiment of the present invention that may be used in place of the cushion assembly of FIG. 4.

FIG. 8 is an isometric view of a cushion assembly 30' according to an alternative exemplary embodiment of the present invention that may be used in place of cushion assembly 30. Cushion assembly 30' includes a cushion member 44' coupled to a support ring 46 as described elsewhere herein.

In the present embodiment, cushion member 44' is defined from a unitary piece of soft, flexible, cushiony, elastomeric material, such as, without limitation, silicone, an appropriately soft thermoplastic elastomer, a closed cell foam, or any combination of such materials. Also in the present embodiment, cushion assembly 30' has a generally triangular shape including a bottom region 48', an apex region 50' located opposite bottom region 48', a first side region 52' and a second side region 54' located opposite first side region 52'. As a result, both cushion member 44' and support ring 46 will have associated bottom, apex and first and second side regions.

As described in greater detail below, cushion member 44' employs a partially inverted geometry described elsewhere herein. In particular, at apex region 50', first side region 52' and second side region 54', cushion member 44' has a geometry similar to that shown in FIG. 1A that includes a support portion 66, similar to support portion 12, is located on the inside of a sealing flap 68, similar to sealing flap 14. As will be appreciated, those portions will engage the cheeks and nose bridge areas of the user. However, at bottom region 48', cushion member 44' includes a support portion 56' (similar to support portion 56) having an engagement portion 62' and a sealing flap 58' (similar to sealing flap 58), wherein sealing flap 58' is located on the inside of support portion 56' closer to the longitudinal axis of cushion assembly 30'. As will be appreciated, that engagement portion 62' will engage the region between the upper lip and nose of the user. Thus, cushion member 44' includes transition regions 70 where it transitions from a traditional to an inverted geometry.

In the exemplary embodiment, support portion 56' including engagement edge 62' is made of a material having a durometer of 00 to 60 on the Shore 00 scale, and has a thickness of 2 mm to 15 mm. In addition, because support portion 56' is located below and outside of the inner sealing flap 58', engagement edge 62' is able to have a flatter profile as described elsewhere herein (e.g., ±30 degrees or substantially flat). Furthermore, by positioning sealing flap 58' inside of support portion 56', sealing flap 58' is able to be made much shorter than prior art sealing flaps (e.g., 15 mm or less or 5 mm or less). Finally, sealing flap 58' may be made of a material having a durometer of 00-60 Shore 00 and/or an elongation of approximately 500-1500%, and may have a reduced thickness (e.g., 0.25 mm to 2 mm).

Figure 9:
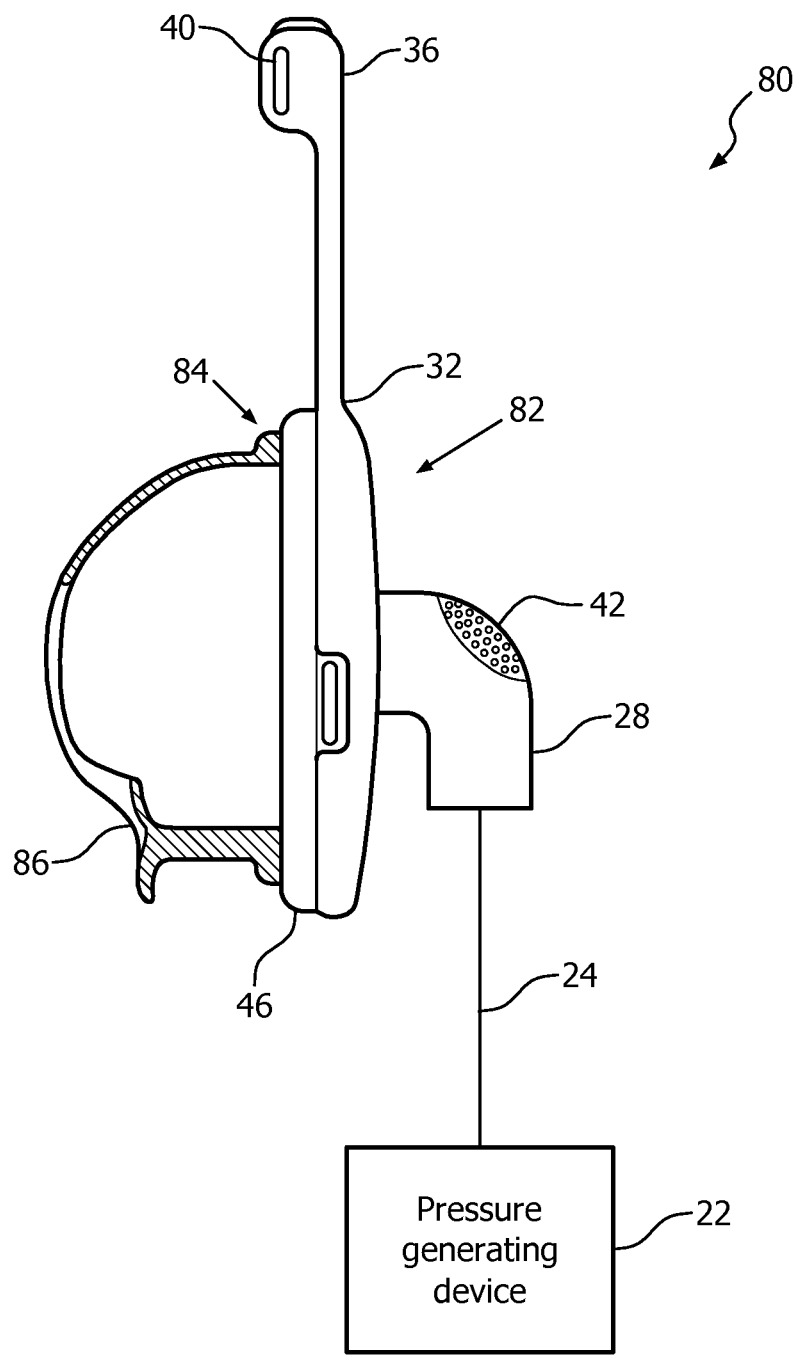
FIG. 9 is a schematic diagram of a system adapted to provide a regimen of respiratory therapy to a patient according to an alternative exemplary embodiment of the invention.

A system 80 adapted to provide a regimen of respiratory therapy to a patient according to an alternative exemplary embodiment of the invention is generally shown in FIG. 9. System 80 includes a number of the same components as system 20 (FIG. 2), and like parts are labeled with like reference numerals. System 80 includes an alternative patient interface device 82 that employs an alternative cushion assembly 84 described below.

Figure 10:
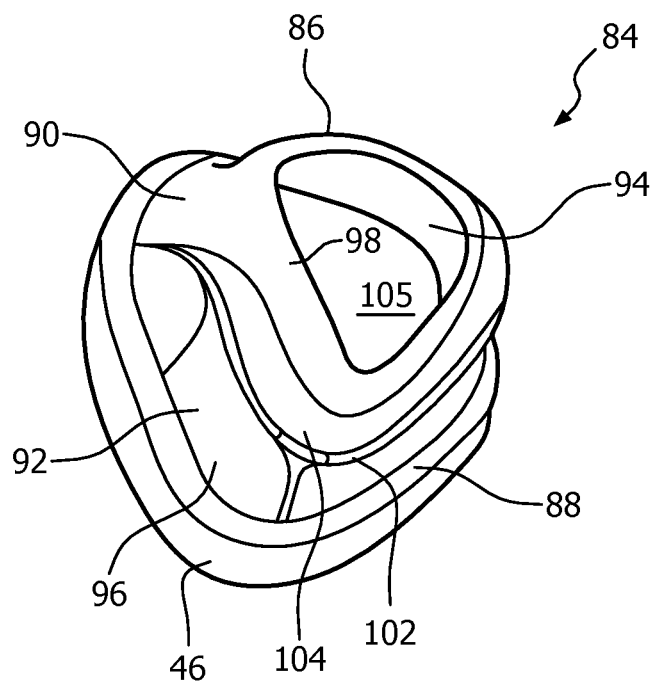
FIG. 10 is an isometric view.
Figure 11:
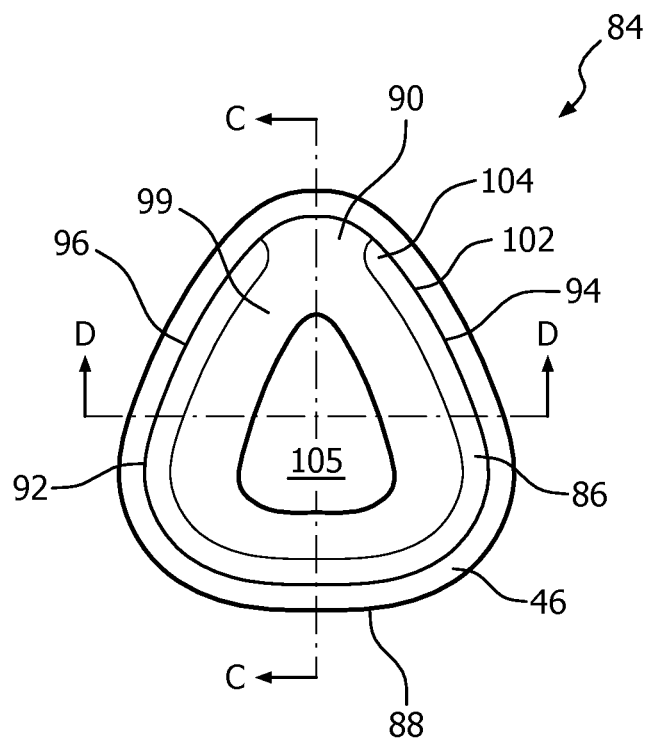
FIG. 11 is a front plan view of a cushion assembly of a patient interface device of the system of FIG. 9.
Figure 12:
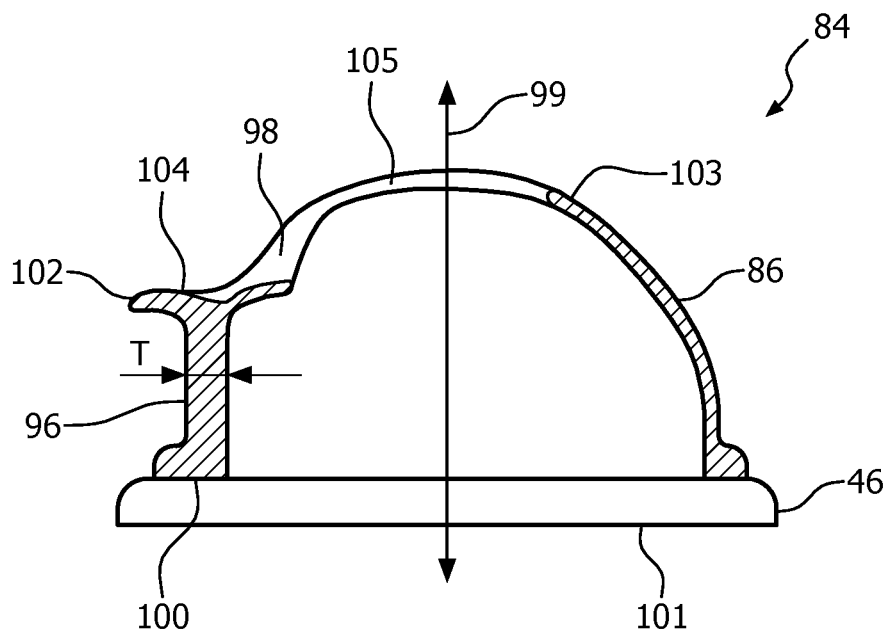
FIG. 12 is a cross-sectional view of the cushion assembly of FIG. 10 taken along lines C-C of FIG. 11.
Figure 13:
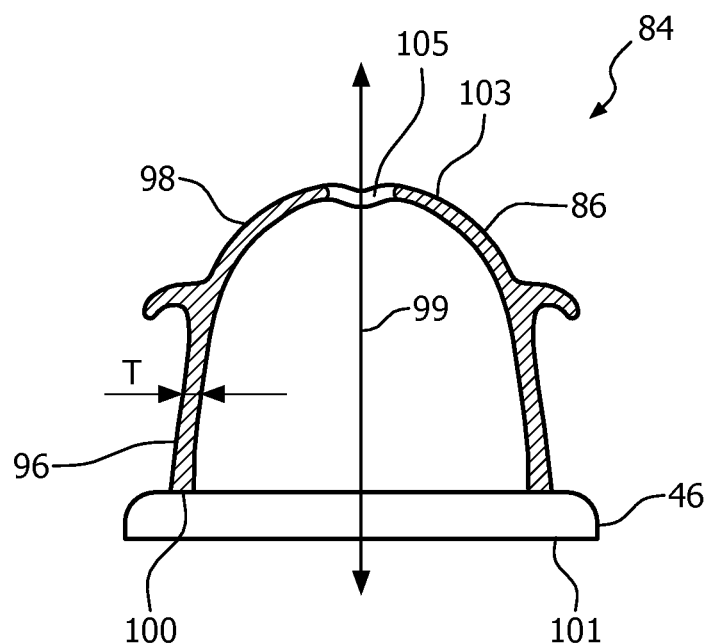
FIG. 13 is a cross-sectional view of the cushion assembly of FIG. 11 taken along lines D-D of FIG. 11.

FIG. 10 is an isometric view and FIG. 11 is a front plan view of cushion assembly 84 according to the exemplary embodiment. In addition, FIG. 12 is a cross-sectional view of cushion assembly 84 taken along lines C-C of FIG. 11 and FIG. 13 is a cross-sectional view of cushion assembly 84 taken along lines D-D of FIG. 11. Cushion assembly 84 includes a cushion member 86 coupled to a support ring 46 as described elsewhere herein.

In the exemplary embodiment, cushion member 86 is defined from a unitary piece of soft, flexible, cushiony, elastomeric material, such as, without limitation, silicone, an appropriately soft thermoplastic elastomer, a closed cell foam, or any combination of such materials. Also in the exemplary embodiment, cushion assembly 84 has a generally triangular shape including a bottom region 88, an apex region 90 located opposite bottom region 88, a first side region 92 and a second side region 94 located opposite first side region 92. As a result, both cushion member 86 and support ring 46 will have associated bottom, apex and first and second side regions.

Cushion member 86, like cushion member 44, is inverted as compared to the traditional geometry described elsewhere herein. In particular, cushion member 86 includes a support portion 96 and a sealing flap 98, wherein sealing flap 98 is located on the inside of support portion 96 closer to a longitudinal axis 99 (FIGS. 12 and 13) of cushion assembly 84 (longitudinal axis 99 extends from the rear 101 of cushion assembly 384 where cushion assembly 84 attaches to frame member 32 to the front 103 of cushion assembly 84, and thus defines the general direction in which gasses flow through cushion assembly 84). In other words, support portion 96 is located below and outside of the inner sealing flap 98. Sealing flap 98 extends in a cantilevered fashion from support portion 96 and defines an orifice 105 structured to receive the nose of the user. As described in greater detail herein, this inverted geometry creates minimal landing on the user's face while achieving contact of support portion 96 and a sealing flap 98, all without encroaching the nares, thereby leaving a free and clear air path.

As seen in FIGS. 12 and 13, support portion 96 in the exemplary embodiment comprises an outer wall of cushion member 86 that extends outwardly from support ring 46 (i.e., generally parallel to longitudinal axis 99 and generally perpendicular to the plane defining rear 101 of cushion member 86 where cushion member 86 attaches to support ring 46). In addition, in the exemplary embodiment, support portion 96 extends along first side region 92, bottom region 88, and second side region 94. Support portion 96 includes a bottom edge 100 that is adjacent and directly coupled to support ring 46. Support portion 96 further includes a cantilevered portion 102 that extends from a top edge 104 of support portion 96 that is opposite bottom edge 100. Cantilevered portion 102 extends in a direction that is opposite sealing flap 98 (i.e., away from the center of orifice 105). In one embodiment, cantilevered portion 102 is curved. In another embodiment, cantilevered portion 102 extends outwardly (away from the center of orifice 105) in a generally linear fashion at an angle with respect to a second plane that is parallel to the plane defining rear 101 of cushion member 86, wherein that angle is less than or equal to +30 degrees and greater than or equal to −30 degrees. In one particular exemplary embodiment, cantilevered portion 102 is "substantially flat," which as used herein shall mean that it extends in a generally linear fashion at an angle with respect to the second plane that is less than or equal to +5 degrees and greater than or equal to −5 degrees (i.e., it inclines or declines no more than 5 degrees in either direction).

Cantilevered portion 102 and top edge 104 together provide an engagement edge that is structured to engage the face of the user when patient interface device 82 is donned by the user. In particular, in the present embodiment, the portion of the engagement edge at first side region 92 will engage one cheek of the user, the portion of the engagement edge at bottom region 88 will engage the region between the upper lip and nose of the user, and the portion of the engagement edge at second side region 94 will engage the other cheek of the user. In the exemplary embodiment, support portion 96 is made of a material having a durometer of 40 to 90 on the Shore 00 scale, and has a thickness (T in FIGS. 12 and 13) of 1 mm to 6 mm.

Furthermore, by positioning sealing flap 98 inside of support portion 96, sealing flap 98 is able to be made much shorter than prior art sealing flaps (e.g., 15 mm or less or 5 mm or less). Also, sealing flap 98 may be made of a material having a durometer of 00-60 Shore 00 and/or an elongation of approximately 500-1500%, and may have a reduced thickness (e.g., 0.25 mm to 2 mm).

In a further alternative embodiment, support portion 96 as just described may be provided only at bottom region 88, with a geometry similar to that shown in FIG. 1A being provided at apex region 90, first side region 92 and second side region 94. Such an embodiment would thus be a partially inverted geometry. In such an embodiment, support portion 96 will engage the region between the upper lip and nose of the user.

While the inverted geometries provided herein have been described in connection with embodiments where the geometries are provided only at the upper lip or at the upper lip and sides of the cushion, it will be understood that that is meant to be exemplary only and not limiting. Rather, it will be understood that the inverted geometries provided herein may be provided anywhere around a cushion (e.g., at strategic locations around the cushion, such as, without limitation, only at the cheeks (sides) and not the upper lip, or only at partial, short locations at the cheeks and/or the upper lip).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for a patient interface device, comprising:
   a support portion having a bottom edge and an engagement edge located opposite the bottom edge at a top most portion of the support portion, the bottom edge lying in a first plane, the engagement edge being structured to engage a face of a user when the patient interface device is donned by the user, wherein the engagement edge extends at an angle with respect to a second plane that is parallel to the first plane that is less than or equal to +30 degrees and greater than or equal to −30 degrees; and
   a sealing flap having a proximal end attached directly to the engagement edge of the support portion at an inner edge of the engagement edge of the support portion, the sealing flap extending in a cantilevered fashion inwardly from the inner edge and toward a longitudinal axis of the cushion, wherein an entirety of the sealing flap extends upwardly from the engagement edge in a direction away from the bottom edge, wherein a length of the sealing flap measured from the proximal end thereof located at a point where the sealing flap is directly attached to the support portion to a distal end thereof located at a point where the sealing flap defines an orifice is 15 mm or less, wherein the cushion has a generally triangular shape including a bottom region, an apex region located opposite the bottom region, a first side region, and a second side region located opposite the first side region, wherein the support portion and the sealing flap are provided along a length of the bottom region and along at least a portion of a length of the first side region and the second side region but not along the apex region.

2. The cushion according to claim 1, wherein the length of the sealing flap measured from the proximal end thereof to the distal end thereof is 5 mm or less.

3. The cushion according to claim 1, wherein the engagement edge is substantially flat.

4. The cushion according to claim 1, wherein the support portion is made of a material having a durometer of 00 to 60 on the Shore 00 scale and has a thickness of 2 mm to 15 mm.

5. The cushion according to claim 1, wherein the sealing flap has a thickness of 0.20 mm to 2 mm.

6. The cushion according to claim 5, wherein the thickness of the sealing flap is 0.20 mm to 0.40 mm.

7. The cushion according to claim 6, wherein the sealing flap is made of a material having a durometer of 00-60 Shore 00 and an elongation of approximately 500 to 1500%.

8. A cushion for a patient interface device, comprising:
   a support portion having a bottom edge and an engagement edge located opposite the bottom edge at a too most portion of the support portion, the bottom edge lying in a first plane, the engagement edge being structured to engage a face of a user when the patient interface device is donned by the user, wherein the engagement edge extends at an angle with respect to a second plane that is parallel to the first plane that is less than or equal to +30 degrees and greater than or equal to −30 degrees; and
   a sealing flap having a proximal end attached directly to the engagement edge of the support portion at an inner edge of the engagement edge of the support portion, the sealing flap extending in a cantilevered fashion inwardly from the inner edge and toward a longitudinal axis of the cushion, wherein an entirety of the sealing flap extends upwardly from the engagement edge in a direction away from the bottom edge, wherein a length of the sealing flap measured from the proximal end thereof located at a point where the sealing flap is directly attached to the support portion to a distal end thereof located at a point where the sealing flap defines an orifice is 15 mm or less, wherein the cushion has a generally triangular shape including a bottom region, an apex region located opposite the bottom region, a first side region, and a second side region located opposite the first side region, wherein the support portion and the sealing flap are provided only along a length of the bottom region, and wherein the apex region, the first side region and the second side region include a second support portion and a second sealing flap, wherein the second support portion is located inside the second sealing flap.

9. The cushion according to claim 8, wherein the length of the sealing flap measured from the proximal end thereof to the distal end thereof is 5 mm or less.

10. The cushion according to claim 8, wherein the engagement edge is substantially flat.

11. The cushion according to claim 8, wherein the support portion is made of a material having a durometer of 00 to 60 on the Shore 00 scale and has a thickness of 2 mm to 15 mm.

12. The cushion according to claim 8, wherein the sealing flap has a thickness of 0.20 mm to 2 mm.

13. The cushion according to claim 12, wherein the thickness of the sealing flap is 0.20 mm to 0.40 mm.

14. The cushion according to claim 13, wherein the sealing flap is made of a material having a durometer of 00-60 Shore 00 and an elongation of approximately 500 to 1500%.

* * * * *